US006730643B2

(12) United States Patent
Chokappa et al.

(10) Patent No.: US 6,730,643 B2
(45) Date of Patent: May 4, 2004

(54) DETERGENT BAR AND A PROCESS FOR MANUFACTURE

(75) Inventors: Dhanraj Kalyansundaram Chokappa, Mumbai (IN); Vinodkumar Ramniranjan Dhanuka, Mumbai (IN); Subhash Shivshankar Mhatre, Mumbai (IN)

(73) Assignee: Unilever Home & Personal Care USA Division of Conopco, Inc., Greenwich, CT (US)

( * ) Notice: Subject to any disclaimer, the term of this patent is extended or adjusted under 35 U.S.C. 154(b) by 23 days.

(21) Appl. No.: 10/197,181

(22) Filed: Jul. 17, 2002

(65) Prior Publication Data

US 2003/0027734 A1 Feb. 6, 2003

(30) Foreign Application Priority Data

Jul. 23, 2001 (IN) .................................. 705/MUM/2001

(51) Int. Cl.[7] .................................................. A61K 7/50

(52) U.S. Cl. ....................... 510/147; 510/141; 510/152; 510/153; 510/155; 510/156

(58) Field of Search ................................ 510/141, 147, 510/152, 153, 155, 156

(56) References Cited

U.S. PATENT DOCUMENTS

| | | | | |
|---|---|---|---|---|
| 2,820,768 | A | 1/1958 | Fromont | |
| 4,206,069 | A | 6/1980 | Borrello | |
| 4,988,453 | A | 1/1991 | Chambers et al. | |
| 5,310,495 | A | 5/1994 | Hill et al. | |
| 5,736,504 | A | 4/1998 | Duan et al. | |
| 2002/0137643 | A1 * | 9/2002 | Abbas | 510/141 |

FOREIGN PATENT DOCUMENTS

| | | | |
|---|---|---|---|
| GB | 2 110711 | A | 3/1983 |
| JP | 570098236 | A | 6/1982 |
| JP | 64000200 | A | 11/1987 |
| JP | 63057699 | A | 3/1988 |
| JP | 040255800 | A | 9/1992 |
| JP | 4328200 | A | 11/1992 |
| JP | 10147800 | A | 6/1998 |
| WO | 93/19159 | A1 | 9/1993 |
| WO | 95/03391 | | 2/1995 |
| WO | 95/03392 | | 2/1995 |

OTHER PUBLICATIONS

WPI 1998–371243 (JP10147800A), nma.
WPI 1992–430193 (JP4328200A), nma.
WPI 1988–108911 (JP63057699A), nma.
WPI 1989–050580 (JP 64000200A), nma.
EPO–Patent Abstracts of Japan —of JP04091011, dated Mar. 24, 1992, 1 p.
International Search Report No. PCT/EP 02/07266 dated Oct. 17, 2002, 4 pp.

* cited by examiner

*Primary Examiner*—Necholus Ogden
(74) *Attorney, Agent, or Firm*—Alan A. Bornstein

(57) ABSTRACT

A transparent soap bar comprising:

(iii) from 30 to 60% by weight of the soap bar of total fatty matter wherein from 1 to 15% by weight is the salt of 12-hydroxystearic acid or a precursor thereof;

(iv) from 20 to 50% by weight of the soap bar of at least one polyhydric alcohol; and (iii) water.

12 Claims, No Drawings

DETERGENT BAR AND A PROCESS FOR MANUFACTURE

The present invention relates to transparent soap compositions The invention more particularly relates to transparent soap compositions comprising the salt of 12-hydroxystearic acid or a precursor thereof. The invention also relates to an improved cast route process for making transparent soap that is energy saving, economical and rapid. The process uses less alcohol during processing and lower maturation times than the conventional cast route for making transparent soap.

Transparent soaps have aesthetic appeal and are perceived to be milder than opaque bars. The soaps are transparent due to the fact that the soap is deposited from an alcoholic solution in a transparent, microcrystalline form.

Transparent soaps are usually prepared by the solvent method or the cast route wherein the dried, conventional form of toilet soap is dissolved in boiling ethanol, or the saponification is carried out in an ethanol-water mixture. A clear solution is thus obtained which is then poured into moulds and cooled. The solidified soap obtained is then matured over many weeks to obtain the desired transparent soap. High levels of ethanol or polyhydric alcohols like glycerol and poly(ethylene glycol) are usually required to achieve good transparency.

The term maturation refers to the slow evaporation of alcohol and water from the soap mass, until the amount of alcohol in the soap is minimal.

In a typical process, fatty acids, typically coconut fatty acid (CNFA), stearic acid, palmitic acid and lauric acid are mixed with a polyhydric alcohol like poly(ethylene glycol) or glycerol. Water and ethanol are added, and the whole mixture is saponified. Other ingredients like common salt, ethylene diamine tetraacetic acid (EDTA), antioxidants and synthetic surfactants like sodium lauryl sulphate (SLS) can be optionally added. The mixture is filtered and then placed in a cooler, typically a Schicht cooler. The bars formed are removed, and the ethanol evaporated over a period of at least four to five weeks. The bars are then cut to a desired shape and stored for two to three weeks until most of the ethanol is removed, and bars with good hardness and transparency are obtained.

The fatty acid content of the final soap so obtained is known as the total fatty matter (TFM), and can vary between 40 and 80%.

Other methods known in the art give translucent soaps. Hence the cast route remains the most popular method of making transparent soap. However, one of the disadvantages of making soap by the cast route is that a large amount of ethanol is used in the process, which can be hazardous. Also, maturation times for making the soap are very long, and can range from 6 to 8 weeks. Hence, there has always been a need in the industry to cut down the maturation time, as well as minimise or eliminate the use of volatile alcohol in the process of manufacture using the conventional cast route, whilst retaining the hardness and transparency of soaps produced by the cast route. Further, the same has to be achieved in an economical manner.

U.S. Pat. No. 4,988,453 (Lever Brothers Company) discloses translucent soap bars comprising 30 to 45% by weight of soap with respect to the total bar, 5 to 15% of a monohydric alcohol and 5 to 15% by weight of a dihydric alcohol by weight of the soap bar. The combination of monohydric alcohol and polyhydric alcohol is said to promote translucency. It is claimed that the process avoids long maturation times.

JP 04328200 (Junsei Sangyo My Skincare Lab) relates to transparent soaps containing 16 to 25% sodium tetradecane sulphonate, 25–30% of a soap substrate, 20–28% propylene glycol, 10–15% glycerol and water. Transparency is said to be imparted by the glycerol or other agents like sucrose and polyols. Ethanol is not used in the process, and the soap is prepared by pouring a molten solution, solidifying through cooling and cutting. It is claimed that the soap eliminates the process of drying and maturation.

JP10147800 (Yotsuba Yuka KK) relates to soap compositions good in transparency, hardness and foaming that can be produced without using ethanol. Anionic surfactants including higher fatty acid salt and an acylamino acid salt, water and a polyhydric alcohol are used in the process.

The transparent soap bars of JP 04328200 and JP10147800 disclose the use of high levels of non-soap detergents that are expensive. Further the transparent soaps of the above patents use high levels of polyhydric alcohols to achieve transparency. Polyhydric alcohols are expensive, and when used at high levels can cause the soap to become soft and sticky. Hence, it is not advantageous to employ these processes to obtain transparent soap bars.

JP 64000200 (Nippon Oils and Fats) relates to preparation of transparent soap by kneading the soap composition by a biaxial kneading extruder and moulding the product obtained into a desired shape. The agent imparting transparency is a polyhydric alcohol. The soap does not require maturation.

WO 9503391 and WO 9503392 (Unichema Chemie B. V.) relate to a process for making transparent or translucent soap in which the soap is subjected to enough mechanical working and shear to induce transparency. Mechanical working and shear can be carried out using a Z-blade mixer, rolling mills or cavity transfer mixers. The soap contains 60 to 80% by weight of an alkali metal soap of saturated or unsaturated fatty acids and from 5 to 20% by weight of polyhydric alcohols and can optionally contain up to 20% hydroxystearic acid.

The above patents deal with mechanical processes to obtain transparent bars. It is known that the cast route is a preferred route and provides for superior transparency than the mechanical route.

U.S. Pat. No. 5,310,495 (Lever Brothers Company) relates to transparent bars said to be of exceptional clarity. The bar comprises a mixture of alkanolammonium and alkali metal fatty acid salts and a liquid solvent system including water and free alkanolamine. The bar does not require the use of expensive fatty acids/oils like castor oil or ricinoleic acid. U.S. Pat. No. 2,820,768 (Fromont) and U.S. Pat. No. 4,206,069 (Borrello) also disclose the use of alkanolammonium soaps including free alkanolamine to provide for transparent soaps.

Alkanolammonium soaps are often used to prepare transparent soaps. Such soaps usually contain free alkanolamine. The process does not use ethanol, and maturation time may also be reduced. However, there are problems with the use of alkanolamines both in terms of safety and cost, and it is desirable to manufacture transparent soap without using alkanolamines.

GB 2110711 (Unilever) relates to detergent bar compositions that contain at least 30% tallow soap and 3 to 30% by weight of a soluble salt of 12-hydroxystearic acid. However, the bars are not transparent soaps.

JP 63057699 (Shiseido) relates to transparent gel compositions that comprise hexagonal crystalline liquid phase of fatty acid soap, polyhydric alcohol and water. The fatty acid can be 12-hydroxystearic acid.

Soap compositions comprising 12-hydroxystearic acid are present in the form of transparent gels or opaque soap compositions. WO 95/03391 and WO 95/03392 disclose processes to make transparent soap compositions comprising 12-hydroxystearic acid, however these are prepared by the mechanical route, the disadvantages of which have been set out earlier.

Thus the prior art does not teach the preparation of transparent soaps by the cast route by a process wherein the use of alcohol is minimised and the maturation times reduced without compromising properties of the soap such as transparency, hardness and good foaming.

The present applicants have now found that the cast route can achieve the same by the saponification of 12-hydroxystearic acid (or hardened castor oil) along with other fatty acids and/or oils in the presence of polyhydric alcohols and water. The alcohol required during saponification is eliminated or greatly reduced by using the process of the invention. The maturation time is also reduced using the process of the invention. Further the total fatty matter can also be reduced as compared to the conventional cast route for making transparent soap.

The soap bars of the invention show good transparency, as well as good hardness and foaming. Other ingredients may be added to the soap without compromising these properties.

Thus the present invention relates to a transparent soap bar composition comprising 30 to 60% of total fatty matter wherein 1 to 15% is the salt of 12-hydroxystearic acid or a precursor thereof, 20 to 50% of at least one polyhydric alcohol and water. The invention thus provides for low TFM transparent soaps. The invention may also relate to a process for making a transparent soap bar comprising the steps of admixing a mixture of a) 12-hydroxystearic acid or a precursor thereof, b) one or more fatty acids and/or oils, c) at least one polyhydric alcohol, d) water, and optionally ethanol, followed by neutralising the mixture and preferably filtering the same, cooling, pouring into a mould and maturing over a period of 0–4 weeks. In the process of the invention, minimal or no ethanol is required to make a transparent soap, and the maturation time is greatly reduced.

The soaps prepared by the process of the invention show good transparency as well as good lather, feel, hardness.

The total fatty matter or TFM is the fatty acid content of the final soap bar.

According to the first aspect of the invention, there is provided a transparent soap bar comprising, with respect to the total weight of the soap bar:

1. 30 to 60% of total fatty matter as herein described wherein 1 to 15% by weight of the soap bar is the metal salts of 12-hydroxystearic acid or a precursor thereof;
2. 20 to 50% of at least one polyhydric alcohol;
3. 5 to 25, preferably 5 to 20% water; and
4. optionally a non-soap detergent active.

According to a further aspect of the invention, there is provided a transparent soap bar comprising, with respect to the total weight of the soap bar:

1. 30 to 60% of total fatty matter as herein described wherein 1 to 15% by weight of the soap bar is the metal salts of 12-hydroxystearic acid or a precursor thereof, wherein the total fatty matter is selected such that the fat charge has an iodine value of from 0 to 20;
2. 20 to 50% of at least one polyhydric alcohol;
3. 5 to 25%, preferably 5 to 20% water; and
4. optionally a non-soap detergent active.

According to the second aspect of the invention, there is provided a process for making the transparent soap bar of the invention comprising the steps of:

a. admixing;
   1. 12-hydroxystearic acid or a precursor thereof and at least one other fatty acid and/or oil;
   2. at least one polyhydric alcohol;
   3. water;
   4. 0–11% of a volatile alcohol by weight of the total mass;
b. neutralising the mixture by using a suitable alkali;
c. optionally adding a suitable non-soap detergent active and a polyhydric alcohol, preferably filtering, cooling, pouring into a suitable mould, followed by maturation over a period of 0–4 weeks;

wherein the volatile alcohol has a boiling point not greater than 90 degrees centigrade.

According to a further aspect of the invention, there is provided a process for making a transparent soap bar of the invention comprising the steps of:

a. admixing:
   1. 12-hydroxystearic acid or a precursor thereof and at least one other fatty acid and/or oil, wherein the fatty matter is selected such that such that the fat charge has a iodine value of from 0 to 20;
   2. at least one polyhydric alcohol;
   3. water;
   4. 0–11% of a volatile alcohol by weight of the total mass;
b. neutralising the mixture by using a suitable alkali;
c. optionally adding a suitable non-soap detergent active and a polyhydric alcohol, preferably filtering, cooling, pouring into a suitable mould, followed by maturation over a period of 0–4 weeks.

In a still further preferred aspect, the process of the invention comprises the steps of:

a. admixing:
   1. stearic acid, palmitic acid, lauric acid, hardened palm kernel oil and 12-hydroxystearic acid, such that the total fatty matter of the total soap bar is 30 to 60% wherein 1 to 15% by weight of the total soap bar is 12-hydroxystearic acid;
   2. 25 to 50% by weight of the total soap bar of poly (ethylene glycol);
   3. 5 to 20% water by weight of the total soap bar;
   4. 0–11% ethanol by weight of the total mass;
b. neutralising the mixture by using a suitable alkali;
c. optionally adding a suitable non-soap detergent active and sorbitol, filtering the mass, cooling, pouring the mass into a suitable mould, followed by maturation over a period of 0–4 weeks.

Throughout the specification, all parts are by weight unless otherwise specified.

By the word transparent is meant that the soap bar is capable of transmitting light there through.

The present invention relates to a transparent soap bar comprising total fatty matter of 30 to 60% by weight of the total soap bar; wherein 1 to 15% by weight of the total soap bar is a metal salt of 12-hydroxystearic acid or a precursor thereof, at least one polyhydric alcohol and water. Preferably the fat charge used to make the transparent soap has a iodine value of from 0 to 20.

The invention also relates to a process to make transparent soap that uses minimal or no alcohol in the process. The process comprises the steps of admixing 12-hydroxystearic acid or a precursor thereof and at least one fatty acid and/or oil, at least one polyhydric alcohol, water and 0–11% of a volatile alcohol by weight of the total mass, neutralising the mixture by using a suitable alkali, optionally adding a suitable non-soap detergent active and a polyhydric alcohol, preferably filtering the mass, cooling, pouring into a suitable mould, followed by maturation over a period of 0–4 weeks.

The transparent soap of the present invention is obtained by saponifying fatty acids or oil or their blends. Suitable fatty acids are the C8–C22 fatty acids. Fatty acids particularly suitable for the invention include stearic acid, lauric acid and palmitic acid. These can also be obtained from plant and/or animal sources, for example tallow fatty acids, palm fatty acids etc.

Resin acids, such as those present in tall oil are also suitable for the invention. Naphthenic acids may also be used for the invention.

The term soap refers to the salts of these fatty acids. Suitable cations include sodium, potassium, zinc, magnesium, alkyl ammonium and aluminium. Sodium is an especially preferred cation.

For a soap having 18 carbon atoms, an accompanying sodium cation will generally amount to about 8% by weight.

It is also possible to saponify oils or their mixtures with fatty acids. Suitable oils for the invention include tallow, tallow stearines, palm oil, palm stearines, soya bean oil, fish oil, rice bran oil, sunflower oil, coconut oil, babassu oil and palm kernel oil. Especially preferred is hardened palm kernel oil.

The fatty acid soaps can also be prepared by a synthetic process e.g. by the oxidation of petroleum or by the hydrogenation of carbon monoxide by the Fischer-Tropsch process.

The total fatty matter of the transparent soap is from 30 to 60%, more preferably from 30 to 50% and most preferably from 35 to 45%.

12-hydroxystearic acid is an essential component of the total fatty matter and is present in an amount of from 1 to 15% by weight of the total soap composition. Hardened castor oil, which contains about 85% 12-hydroxystearic acid esters is suitable for the process of the invention.

Preferably, the fat charge used to make the transparent soap of the invention has an iodine value of from 0 to 20, more preferably from 2 to 15.

Polyhydric alcohols suitable for use according to the invention include poly (ethylene glycol), propylene glycol, glycerol and sorbitol, i.e they include dihydric alcohols and polymers with hydroxyl groups. Especially preferred is a mixture of PEG, propylene glycol and sorbitol. The polyhydric alcohol is suitably added a) before saponification or b) before and after saponification.

Poly(ethylene glycol) used in the invention preferably has a molecular weight of from 200 to 1500.

The polyhydric alcohol is present in an amount of from 20 to 50%, more preferably from 20 to 45% and most preferably from 30 to 40% by weight of the total soap bar.

Prior to the saponification process, volatile alcohol and water are added to the mixture to be saponified. The volatile alcohol is present in an amount of from 0 to 11%, more preferably from 0 to 9%. Ethanol is an especially preferred volatile alcohol.

Saponification may be carried out by using a suitable alkali. Examples include caustic soda and sodium carbonate. Caustic soda is especially preferred. While it is preferable not to use alkanolamines and good transparency can be achieved without using the same, optionally alkanolamines, like triethanolamine, may be added during saponification in the process of the invention.

Non-soap detergent actives are preferably added during the process of the invention. They may be suitably added after the saponification step. Non-soap detergent actives may be chosen from anionic, cationic, zwitterionic, amphoteric surfactants or their mixtures thereof.

The non-soap detergent active is generally chosen from an anionic, nonionic, cationic, zwitterionic detergent active or mixtures thereof. Preferably the amount of the non-soap detergent active does not exceed 20%.

Anionic surfactants that can be used in the soap bars of the invention are non-soap detergents compounds. Especially suitable anionic detergent active compounds are water soluble salts of organic sulphuric reaction products having in the molecular structure an alkyl radical containing from 8 to 22 carbon atoms, and a radical chosen from sulphonic acid or sulphur acid ester radicals and mixtures thereof.

Suitable nonionic detergent active compounds can be broadly described as compounds produced by the condensation of alkylene oxide groups, which are hydrophilic in nature, with an organic hydrophobic compound which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Suitable amphoteric detergent-active compounds that optionally can be employed are derivatives of aliphatic secondary and tertiary amines containing an alkyl group of 8 to 18 carbon atoms and an aliphatic radical substituted by an anionic water-solubilizing group, for instance sodium 3-dodecylamino-propionate, sodium 3-dodecylaminopropane sulphonate and sodium N-2-hydroxydodecyl-N-methyltaurate. Suitable cationic detergent-active compounds are quaternary ammonium salts having an aliphatic radical of from 8 to 18 carbon atoms, for instance cetyltrimethyl ammonium bromide.

Suitable zwitterionic detergent-active compounds that optionally can be employed are derivatives of aliphatic quaternary ammonium, sulphonium and phosphonium compounds having an aliphatic radical of from 8 to 18 carbon atoms and an aliphatic radical substituted by an anionic water-solubilising group, for instance 3-(N-N-dimethyl-N-hexadecylammonium), propane-1-sulphonate betaine, 3-(dodecylmethyl sulphonium) propane-1-sulphonate betaine and 3-(cetylmethylphosphonium) ethane sulphonate betaine.

Further examples of suitable detergent-active compounds are compounds commonly used as surface-active agents given in the well-known textbooks "Surface Active Agents", Volume I by Schwartz and Perry and "Surface Active Agents and Detergents", Volume II by Schwartz, Perry and Berch.

Salts are preferably added after the saponification step. Suitable salts include sodium and potassium salts. Sodium chloride is an especially preferred salt and is preferably used in an amount of from 0.1 to 2%.

Other optional ingredients like anti-oxidants, perfumes, polymers, chelating agents, colourants, deodorants, dyes, emollients, moisturisers, enzymes, foam boosters, germicides, anti-microbials, lathering agents, pearlescers, skin conditioners, solvents, stabilisers, superfatting agents, sunscreens etc. may be added in suitable amounts in the process of the invention, provided the transparency of the soap is retained. Preferably, the ingredients are added after the saponification step and before filtering.

Sodium metabisulphite, ethylene diamine tetra acetic acid (EDTA), borax and ethylene hydroxy diphosphonic acid (EHDP) are preferably added to the formulation.

In a preferred process of the invention 12-hydroxystearic acid or a precursor thereof and one or more fatty acids and/or oils, at least one polyhydric alcohol, water and optionally a volatile alcohol are mixed. The mass is then neutralised by using an alkali, preferably caustic soda. The neutralisation is preferably carried out below 80 degrees centigrade. The completion of neutralisation is monitored by the consumption of alkali. Once the neutralisation is completed, other ingredients may be added to the mass. These include salt, anti-oxidants, non-soap detergent actives, additional polyhydric alcohols, borax, perfume etc.

The mixture is then preferably filtered by suitable means, for example through a filter press. The mixture is then cooled in chilled moulds. Preferably the cooling is carried out by using a Schicht cooler. The bars are typically formed as long cylinders at the end of cooling. The bars are then matured for a period of 0–4 weeks either as such or after cutting into smaller billets or sequentially as bars followed by cut billets. When volatile alcohol is not used in the process, maturation is not required.

In a preferred aspect, the bars obtained from the Schicht cooler are matured for a period of 0 to 2 weeks. The bars are then cut to the requisite shape and size and stamped if required and further matured for a period of 0 to 2 weeks.

The invention will be further described by the following illustrative non-limiting examples. All parts therein are by weight unless otherwise specified.

EXAMPLES

Comparative Example A

In a batch size of 1 kg, 138 g palm kernel fatty acid, 85 g propylene glycol and poly (ethylene glycol) of molecular weight 1500, 161 g stearic and palmitic acid, 40 g lauric acid and butyl hydroxy toluene (0.1 g) were taken in a vessel and heated till the components were in a fluid state. 77 g of ethanol was then added followed by the addition of 47% strength caustic soda lye till the mixture was completely neutralised. 33 g additional ethanol was then added followed by addition of common salt, EDTA, EHDP, sodium lauryl sulphate, sorbitol (70% solution in water), glycerol and sodium metabisulphite (SMBS). The mixing was continued until a clear homogeneous mixture was obtained. The soap mass was then filtered and colour and perfume were added, followed by cooling in a Schicht cooler.

The cast bars were then matured under ambient conditions for a period of 5 weeks. After this maturation the bars were cut to a suitable size and matured for another 2 weeks.

The iodine value of the fatty matter in the soap bar was 4 units.

Example 1

In a batch size of 1 kg, 140 g hardened palm kernel oil, 57 g poly (ethylene glycol) of molecular weight 200, 154 g stearic and palmitic acid mixture, 37 g lauric acid, 33 g hardened castor oil and 42 g of ethanol were taken in a vessel and heated till the components were in a fluid state. Caustic soda lye (47% strength) was added till the mixture was completely neutralised. Common salt, EDTA, EHDP, sodium lauryl sulphate, sorbitol (70% solution in water) and SMBS were then added. The mixing was continued until a clear homogeneous mixture was obtained. The soap mass was then filtered and colour and perfume were added, followed by cooling in a Schicht cooler. The cast bars were then cut to a suitable size and matured for 2 weeks.

The IV of the fatty matter of the soap bar was 2.5.

Example 2

In a batch size of 1 kg, 125 g hardened palm kernel oil, 42 g poly (ethylene glycol) of molecular weight 200, 138 g stearic and palmitic acid mixture, 33 g lauric acid, 69 g hardened castor oil, were taken in a vessel and heated till the components were in a fluid state. Caustic soda lye (47% strength) was added till the mixture was completely neutralised. Common salt, EDTA, EHDP, sodium lauryl sulphate, sorbitol (70% solution in water) and SMBS were then added. The mixing was continued until a clear homogeneous mixture was obtained. The soap mass was then filtered and colour and perfume were added, followed by cooling in a Schicht cooler. The cast bars were then cut to a suitable size and stamped into required shape, without maturation.

The IV of the fatty matter of the soap bar was 2.5.

The composition of the soap bars of Comparative example A and Examples 1 and 2 is shown in Table 1.

The transparency of the soaps is as shown in table 1.

The hardness of the bars was measured. Hardness of the bars is indicated by penetration value. The penetration value was measured using a cone penetrometer the details of which are given below:

Cone type penetrometer
MANUFACTURER: Adair Dutt & Company
RANGE OF MEASUREMENT: 0–40 units
RANGE OF VERIFICATION: 20 in steps of 5

Procedure of measurement: Let the entire mass (comprised of penetrometer needle and standard weight) which just rests on the test sample drop freely and thus penetrate the test mass to a specific distance for a specified period of time and read of this distance as $1/10^{th}$ of mm. Take the average after repeating three times. A higher value indicates a softer bar.

The penetration value of the soap bars of Comparative example A and Examples 1 and 2 is as shown in Table 1.

TABLE 1

| | % of total soap bar | | |
|---|---|---|---|
| | A | 1 | 2 |
| Total TFM | 41 | 39 | 35.5 |
| TFM (other than 12-hydroxystearic acid) | 41 | 35.4 | 28.6 |
| TFM (from 12-hydroxystearic acid) | 0 | 3.6 | 6.9 |
| Polyhydric Alcohols | 33 | 35.4 | 33.5 |
| Sodium lauryl sulphate | 4.5 | 6.2 | 4.2 |
| Water | To 100 | To 100 | To 100 |
| % Ethanol | 11 | 4.5 | 0 |
| Maturation Time (weeks) | 7 | 2 | 0 |
| Transparency | Not Transparent | Transparent | Transparent |
| Hardness | 30 | 26 | 25 |

Thus the invention provides for transparent soap bars with improved hardness. Further the bars of the invention can be prepared by a cast route process that does not use or uses minimal volatile alcohol. The maturation time is also lesser than known processes.

What is claimed is:

1. A transparent soap bar comprising:

(i) from 30 to 60% by weight of the soap bar of total fatty matter wherein from 1 to 15% by weight is the salt of 12-hydroxystearic acid or a precursor thereof;

(ii) from 20 to 50% by weight of the soap bar of at least one polyhydric alcohol; and (iii) water.

2. A soap bar according to claim 1 wherein the fatty matter is selected from $C_{8-22}$ fatty acids.

3. A soap bar according to claim 1 wherein the total fatty matter is present in an amount of from 30 to 50% of the soap bar.

4. A soap bar according to claim 1 wherein the fat charge to make the soap has an iodine value of from 0 to 20.

5. A soap bar according to claim 1 wherein the polyhydric alcohol is selected from the group consisting of: polyethylene glycol, propylene glycol, glycerol and sorbitol and mixtures thereof.

6. A soap bar according to claim 1 further comprising a non-soap detergent active selected from anionic, nonionic, cationic, zwitterionic detergent actives and mixtures thereof.

7. A method of manufacturing a transparent soap bar comprising the steps of:

(a) admixing a fatty matter mixture of 12-hydroxystearic acid or a precursor thereof, at least one other fatty acid and/or oil, at least one polyhydric alcohol, water and from 0 to 11% by weight of the total mass of a volatile alcohol wherein the volatile alcohol has a boiling point not greater than 90° C.;

(b) neutralising the mixture using alkali, cooling; and (c) pouring into a mould and maturing over a period of from 0 to 4 weeks.

8. A method according to claim 7 wherein non-soap detergent active and additional polyhydric alcohol are added following neutralisation.

9. A method according to claim 7 wherein the fatty matter is selected such that the fat charge has an iodine value of from 0 to 20.

10. A soap bar according to claim 1 wherein the fatty matter is selected from stearic, lauric and palmitic acid, resin and naphthenic acids.

11. A soap bar according to claim 1 wherein the total fatty matter is present in an amount of from 35 to 45% by weight of the soap bar.

12. A soap bar according to claim 1 wherein the fat charge to make the soap has an iodine value of from 2 to 15.

* * * * *